(12) United States Patent
 Sidebotham

(10) Patent No.: US 9,370,427 B2
(45) Date of Patent: Jun. 21, 2016

(54) BONE-COMPLIANT FEMORAL STEM

(76) Inventor: Christopher G. Sidebotham, Mendham, NJ (US)

( * ) Notice: Subject to any disclaimer, the term of this patent is extended or adjusted under 35 U.S.C. 154(b) by 1417 days.

(21) Appl. No.: 11/786,831

(22) Filed: Apr. 13, 2007

(65) Prior Publication Data

US 2008/0255675 A1    Oct. 16, 2008

(51) Int. Cl.
| | |
|---|---|
| *A61F 2/36* | (2006.01) |
| *A61F 2/30* | (2006.01) |
| *A61L 27/06* | (2006.01) |
| *A61L 27/30* | (2006.01) |
| *A61L 27/34* | (2006.01) |
| *B22F 7/00* | (2006.01) |
| *A61F 2/46* | (2006.01) |
| *B22F 3/24* | (2006.01) |

(52) U.S. Cl.
CPC .......... *A61F 2/30907* (2013.01); *A61F 2/3662* (2013.01); *A61L 27/06* (2013.01); *A61L 27/30* (2013.01); *A61L 27/34* (2013.01); *B22F 7/004* (2013.01); *A61F 2/3094* (2013.01); *A61F 2/30767* (2013.01); *A61F 2/36* (2013.01); *A61F 2/367* (2013.01); *A61F 2/3676* (2013.01); *A61F 2002/30013* (2013.01); *A61F 2002/30014* (2013.01); *A61F 2002/30064* (2013.01); *A61F 2002/30138* (2013.01); *A61F 2002/30322* (2013.01); *A61F 2002/30703* (2013.01); *A61F 2002/30919* (2013.01); *A61F 2002/30929* (2013.01); *A61F 2002/30957* (2013.01); *A61F 2002/30967* (2013.01); *A61F 2002/30968* (2013.01); *A61F 2002/30971* (2013.01); *A61F 2002/30973* (2013.01); *A61F 2002/3625* (2013.01); *A61F 2002/4631* (2013.01); *A61F 2230/0017* (2013.01); *A61F 2250/0018* (2013.01); *A61F 2250/0024* (2013.01); *A61F 2250/0026* (2013.01); *A61F 2310/00023* (2013.01); *A61F 2310/00029* (2013.01); *A61F 2310/00407* (2013.01); *A61F 2310/00413* (2013.01); *A61F 2310/00491* (2013.01); *A61F 2310/00544* (2013.01); *B22F 2003/242* (2013.01); *B22F 2003/248* (2013.01); *B22F 2998/10* (2013.01); *B22F 2999/00* (2013.01)

(58) Field of Classification Search
CPC   A61F 2/367; A61F 2/3662; A61F 2220/0033
USPC ........................................... 623/23.15, 23.34
See application file for complete search history.

(56) References Cited

U.S. PATENT DOCUMENTS

| | | | | |
|---|---|---|---|---|
| 3,938,198 | A | * | 2/1976 | Kahn et al. ................. 623/22.15 |
| 4,808,186 | A |   | 2/1989 | Smith ............................. 623/23 |
| 4,978,358 | A | * | 12/1990 | Bobyn ....................... 623/23.34 |
| 4,990,161 | A |   | 2/1991 | Kampner ........................ 623/16 |

(Continued)

*Primary Examiner* — Bruce E. Snow
*Assistant Examiner* — Melissa Hoban
(74) *Attorney, Agent, or Firm* — Klarquist Sparkman, LLP

(57) ABSTRACT

A femoral stem for canines or humans is made bone-compliant by use of a thick sintered titanium body in a proximal bone contacting region and a polymeric or ceramic body in a distal bone contacting region of the femoral stem. An elastic modulus is thereby engineered to match that of bone tissue. The porous sintered titanium body is created by sintering spheres of titanium. It is bonded to a central solid biocompatible metallic body by diffusion bonding. The distal region has a biocompatible polymeric body or biocompatible cement body. When compression molded the distal region develops an elastic modulus matching that of bone tissue. The proximal region has a porosity designed to encourage bone ingrowth.

8 Claims, 4 Drawing Sheets

(56) References Cited

U.S. PATENT DOCUMENTS

| | | | |
|---|---|---|---|
| 5,314,492 A | 5/1994 | Hamilton et al. | 623/23 |
| 5,316,550 A | 5/1994 | Forte | 623/23 |
| 5,443,512 A | 8/1995 | Parr et al. | 623/16 |
| 5,514,184 A | 5/1996 | Doi et al. | 623/23 |
| 5,591,233 A | 1/1997 | Kelman et al. | 623/16 |
| 5,733,338 A | 3/1998 | Kampner | 623/16 |
| 5,935,172 A | 8/1999 | Ochoa et al. | 623/18 |
| 6,228,123 B1 | 5/2001 | Dezzani | 623/23.32 |
| 6,312,473 B1 | 11/2001 | Oshida | 623/23.55 |
| 6,436,148 B1 * | 8/2002 | DeCarlo et al. | 623/23.15 |
| 6,656,226 B2 | 12/2003 | Yoon | 623/23.23 |
| 6,887,278 B2 | 5/2005 | Lewallen | 623/22.11 |
| 6,913,623 B1 | 7/2005 | Zhu | 623/23.15 |
| 2004/0102854 A1 | 5/2004 | Zhu | 623/23.15 |
| 2004/0111160 A1 * | 6/2004 | Evans et al. | 623/17.14 |
| 2004/0260398 A1 * | 12/2004 | Kelman | 623/19.11 |
| 2005/0143837 A1 * | 6/2005 | Ferree | 623/23.25 |
| 2006/0276906 A1 * | 12/2006 | Hoag et al. | 623/23.34 |
| 2007/0150068 A1 * | 6/2007 | Dong et al. | 623/22.32 |

* cited by examiner

PRIOR ART

Fig. 3a
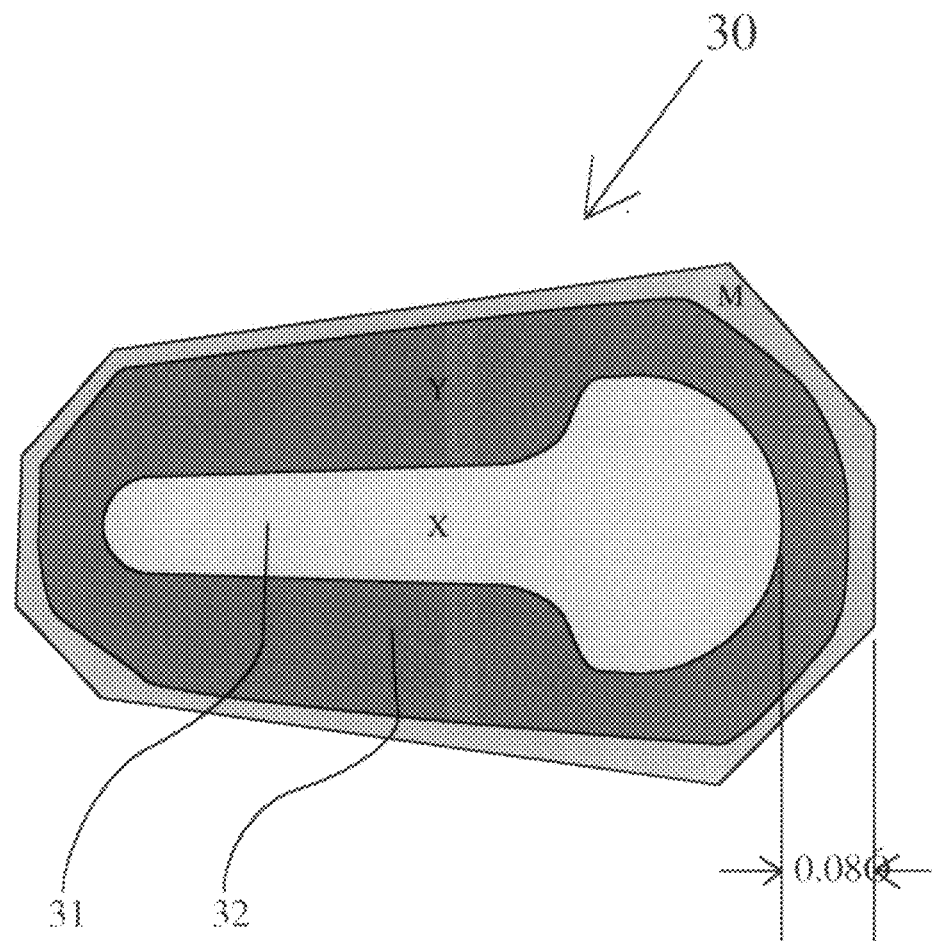
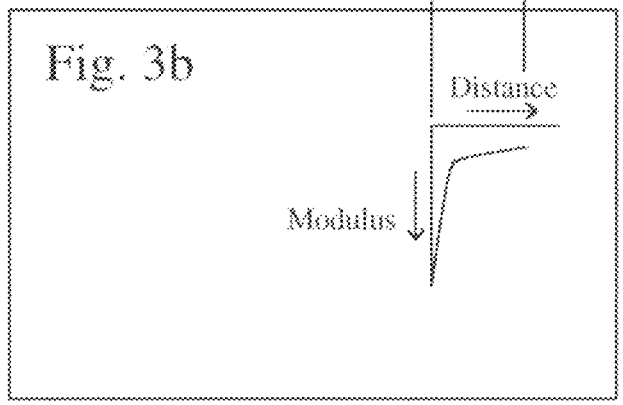
Fig. 3b

BONE-COMPLIANT FEMORAL STEM

BACKGROUND OF THE INVENTION

1. Field of the Invention

The present invention relates to implantable bone prostheses; and, more particularly, to a bone-compliant femoral stem for canines or humans having compatibility with natural bone.

2. Description of the Prior Art

Many patents address issues related to canine femoral and/or human femoral stems. Some patents address adding geometrical features or cracks within the femoral stem to reduce the stiffness of the femoral stem and bring it closer to the stiffness of bone tissue.

U.S. Pat. No. 4,808,186 to Smith discloses a controlled stiffness femoral hip implant for use in the hip or other appropriate body joint. In a hip, a ball member fixed to the femur is rotatably engaged with a cup-shaped socket member fixed to the acetabulum of the pelvic bone. The ball member is mounted on one end of a femoral component, which has an elongated stem receivable in the intramedullary canal of the femur. The stem has a longitudinal channel, which lies in the coronal plane when the stem is in the implanted condition. The thickness of the stem channel is variable between the proximal and distal ends so as to affect the moment of inertia at any given location along its length to achieve stem flexibility, which substantially correlates to the flexibility of the bone. The medial side of the length of the implant is milled out to form a channel shaped stem cross section. The amount of material removed determines the resulting decrease in stiffness of the implant. The outside geometry remains substantially unchanged with the exception of the open channel on the medial side of the implant. Because of the reduction of the moment of inertia of the implant stem, it is more flexible. It also exhibits higher stem stresses upon loading of the implant. Therefore, a careful balance must be achieved between the amount of material removed from the stem and the expected stress levels expected by the particular size implant. However, this milling or material removal operation correspondingly decreases the load carrying capacity of the stem and its flexure behavior is subject to buckling and other non-uniform deformation mechanisms. At the contact location between bone and the implant, the modulus or stiffness has a very large change preventing proper load transfer to the bone. This, in turn, leads to crack formation at the bone-implant interface.

U.S. Pat. No. 4,990,161 to Kampner discloses an implant with resorbable stem, providing a biodegradable anchor selected from the group consisting of polyesters of glycolic acid, polyesters of lactic acid, polyamides of alpha-amino acids, unmodified polymers, modified polymers, calcium hydroxyapatite, tricalcium phosphate or polylactic acid for a permanent implant of a bone joint, e.g. hip, shoulder, knee or finger. The biodegradable anchor is an elongated member having an exterior surface, which tightly engages with a cavity in the bone and is substantially immovable within the cavity upon implant. The anchor is secured by means of a non-resorbable attachment to the permanent implant. This implant has a metallic nonresorbable permanent implant, which is covered by a resorbable anchor that is attached to permanent implant by non-resorbable attachment. The implant fits tightly into a bone cavity. As the resorbable anchor biodegrades, bone ingrowth occurs and the implant is permanently attached to the bone tissue. At this stage, the function of the permanent implant is over and the biodegraded anchor takes all the load and does not stress the bone tissue. The anchor is attached to the permanent implant by non-resorbable attachments. However, as the biodegradable anchor deteriorates and bone regrowth occurs, the anchor and its attachment is weakened. During this interim healing period, the implant is clearly unstable and is subject to movement causing bone-healing problems.

U.S. Pat. No. 5,314,492 to Hamilton et al. discloses a composite prosthesis. The composite stem for a prosthesis, particularly a hip prosthesis, includes a metal core and a fiber reinforced composite shell surrounding the core to provide modulus values that are similar to bone. The composite shell is composed of braided high tensile strength fibers and a bio-compatible thermoplastic resin having substantially equal strength in all directions i.e. isotropic. The shell comprises between 40 and 75 weight percent fiber and 25 to 60 weight percent resin. The stiffness of the prosthesis can be varied along the length of the stem. The metal core contributes to between 5 and 25 percent of the total flexural stiffness of the stem. The composite prosthesis is said to minimize the modulus mismatch of the stem portion of the component with the cortical shell of the femur. In use, the stiffness of the inner member (prosthesis) of the femur-prosthesis combination is said to be minimized; this forces the outer member (cortical shell) to carry a greater portion of the load and react closer to the normal physiological manner thereby reducing the problem of bone resorption. The composite prosthesis disclosed by the '492 patent comprises a metal core, fiber reinforced isotropic polymeric composite shell. The modulus of the composite shell is adjusted to be nearly equal to that of natural bone tissue. There is no bond between the polymeric composite shell and the metal core. Therefore, a separation may occur between the polymeric shell and the metal core, even when the composite shell attaches to bone tissue. Therefore, it is not clear how the metal provides any load bearing support.

U.S. Pat. No. 5,316,550 to Forte discloses a prosthesis having a flexible intramedullary stem. The metallic prosthesis implant for a hip or other joint has an intramedullary stem that has flexibility. Bending and torsional deformation under the influence of active load forces are comparable to that of the surrounding bone. The stem has a tapered bore that longitudinally extends from the proximal end to the distal end. In a second embodiment, the stem has a slit, the width of which also tapers from the proximal end to the distal end providing flexibility to the stem. This flexibility therefore distributes the loading forces from the joint more uniformly over the supporting cortical bone with the result that bone degeneration from stress shielding is minimized or eliminated. The stem of the flexible intramedullary stem has a taped bore providing progressively decreasing stem wall thickness from the proximal and distal end. In a second embodiment a slit is also provided which has a varying width in one side of the wall of the stem with a tapered bore. Both these features provide flexibility to the stem. The decreased wall thickness of the stem at the distal end may result in buckling or collapse of the stem during torsional or bending deformation. The presence of slit complicates the deformation behavior since the slit can open out under load. In any case, the modulus of the metallic stem member is essentially the same as the metal, and any bone contacting the metal surface is subject to shear separation. The configuration of the tapered bore and slits is said to improve the bending and torsional deformation of the stem when loaded.

U.S. Pat. No. 5,443,512 to Parr et al. discloses an orthopaedic implant device. The orthopaedic implant device is formed from a combination of different materials. It includes a body metal component and a porous metal surface layer for intimate contact with bone. Also included is a polymer in the form of a casing that includes adhesive characteristics for attachment to the body metal component and the porous metal layer. The body is a metal made from cobalt chrome and the porous metal surface layer is made from titanium. The preferred polymer casing is polyaryletherketone. This polymer manifests aggressive adhesive characteristics to the metallic surface of the cobalt chrome and the titanium following transformation to a heated state. The orthopaedic implant device contains a titanium metal core to which a porous layer is secured using PAEK polymeric adhesive. Such adhesive is said to produce a strong bond between the titanium core and the titanium porous layer. There is no disclosure relating to the elastic modulus of the porous layer infiltrated with a PAEK polymer. The elastic modulus of the porous layer is expected to be high and anisotropic due to the orientation of the titanium fibers in the porous body and its bond to a polymer. Therefore, its contact with bone tissue will result in shear separation at the interface.

U.S. Pat. No. 5,514,184 to Doi et al. discloses an artificial joint having a porous portion. The total hip replacement type artificial joint comprises a stem and a socket. The stem is provided with a head at the upper end and comprises a porous portion as an upper portion. A protector is located under the porous portion at the same height as the porous surface of the porous portion. An intermediate portion, which underlies the porous portion, has a trapezoidal cross section. A lower portion, which underlies the intermediate portion, has a circular cross section. The protector is provided along the peripheral edge of the outer cup and at the same height as a porous surface of the cup. Such arrangement is said to prevent dropout of the particles from the porous surfaces at the time of insertion into bones of a living body and permit the joint to bear the patient's weight imposed after an operation. A porous portion protector is provided at the same surface level as the porous portion to capture any particles that may drop off from the porous portion when the artificial hip joint is inserted into a surgically prepared bone cavity. There is no means provided to provide a bone-compliant joint since all the materials used for the artificial hip joint are very high modulus metallic materials. Since the disclosure anticipates the drop out of the particles from the porous coating, the particles are not metallurgically bonded to the stem and the coating is thin, not a thick coating capable of grading the modulus. The assembly of particles provide no elastic modulus representing load carrying capability, since they fall apart easily.

U.S. Pat. No. 5,591,233 to Kelman et al. discloses metal/composite hybrid orthopedic implants. The hybrid implant comprises an intraosseous metal portion and an intraosseous composite portion. The composite portion is comprised of filaments nonlinearly disposed within a polymer matrix to produce a structure of variable modulus along its length. The composite portions may be secured to the metal portion by a taper lock, an adhesive joint, or a shrink fit joint. This metal/composite hybrid orthopedic implant comprises an intraosseous metal portion and an intraosseous composite portion. The composite portion is comprised of filaments nonlinearly disposed within a polymer matrix to produce a structure of variable modulus along its length. Neither the metallic portion nor the composite portion with fibers in a polymeric matrix have elastic modulus similar to that of natural bone. Besides, the fibers in the composite portion are longitudinally oriented and as result the elastic modulus varies as a function of direction.

U.S. Pat. No. 5,733,338 to Kampner discloses an implant having a reinforced resorbable stem. A prosthetic implant for a bone joint has an anchor formed of a resorbable sleeve reinforced with a nonresorbable core. Initially, the resorbable layer gives secure anchorage of the stem with an interference fit equivalent to that obtainable with the current state of the art in prosthetic joint replacement. Selected surface portions of the permanent implant component are porous to permit and direct bony attachment. After an optimal period of time elapses to permit sufficient bony attachment around the permanent, porous implant component, the polymer surrounding the metal core of the anchor slowly degrades and ultimately disappears. As a result, only the small diameter nonresorbable core remains in the medullary cavity of the bone. Although a small diameter core remains permanently within the medullary canal, no load bearing occurs through that core because it is spaced apart from cortical bone and, therefore, does not come in contact with the surrounding cortical bone structure. The core becomes essentially nonfunctional and the bone does not "realize" that any stem is actually present. In biomechanical terms only the permanent implant component forming the articulating surface of the joint remains as a permanent functional component and it is the only artificial component across which stresses are being transferred. Thus, the '338 disclosure provides an implant with an anchor including a nonresorbable core surrounded by a resorbable sleeve. The implant has a central non-absorbable metallic core surrounded by an anchor made from resorbable material. The anchor creates an interference fit between the implant and the bone cavity and slowly disintegrates as the bone ingrowth occurs. At this point, the central metallic core becomes detached and no longer carries any load allowing the bone ingrowth to carry all the loading. This method creates a dangerous situation when the implant is first incorporated since the metallic core is not in any manner attached to the anchor. Moreover, the ingrowth of the bone into the anchor progressively destroys the integrity of the resorbable layer, and the bone structure is yet to be built completely for load sharing. The presence of a non-load carrying metallic core reduces the overall cross section of the bone reducing its load capacity.

U.S. Pat. No. 5,935,172 to Ochoa et al. discloses a prosthesis having a variable fit and strain distribution. The joint prosthesis comprises a metallic body having a plurality of negative surface features such as through-slots, deep grooves, tunnels or pits, or valleys defined between projecting fingers or flutes. The metallic body constitutes the structural component of the prosthesis, such as a shell, plate or stem. A second bio-absorbable component filling at least some of the negative surface feature attaches to and extends the body to provide both a fit and a change in the initial stiffness. The bio-absorbable component protrudes from an external surface of the femoral stem by a distance of about 0.001 inches to 0.250 inches. The second part provides a time-evolving structural coupling, such that the prosthesis initially fits the patient's remnant bone to provide rigid fixation, while the mechanical properties shift with time in vivo to change its contact or loading characteristics. The femoral stem joint prosthesis may be modular and the first, or structural component, accommodates bio-absorbable second components of varying geometries and dimensions which fit a range of bore sizes, and achieve different stiffnesses or strengths affecting load or strain distribution. This prosthesis with variable fit and strain distribution is a two-part prosthesis. A first part of the prosthesis is made of bio-compatible metal, which is the metallic support member. A second sleeve inserted over the first member is made of biosorbable material. The tip of the prosthesis is produced as a series of separated spikes with the biosorbable material wedged therebetween. As the bone grows into this distal region, the reduced stiffness at the distal end is realized. Therefore, the prosthesis is initially tight fitting and becomes more stiffness friendly as the biosorbable material is absorbed by the growing bone. There is no reduction in modulus incompatibility of the bone with the prosthesis when it is implanted; rather a large time needs to be spent before the biosorbable distal end of the implant is absorbed.

U.S. Pat. No. 6,228,123 to Dezzani discloses a variable modulus prosthetic hip stem. The variable modulus prosthetic hip stem is insertable in an intramedullary cavity to support an articulation component, which includes a proximal neck portion and a distal root portion. The proximal neck is solid compatible metal such as titanium, cobalt chromium, stainless steel and extends for a length effective to reach into the cavity and couple to surrounding bone for load bearing engagement. The distal root portion includes a stranded cable of 10 mil cross section wires, which fills the bone cavity but flexes to avoid significant transfer of bending stresses. The cable is tightly bunched at its junction with the neck, providing a transitional degree of stiffness to its distal part, which is significantly more flexible and bends to accommodate natural displacement of the surrounding bone. The prosthesis has a section modulus characterized by three distinct regions. The proximal end region has the largest cross section and presents a stiff modulus of solid material, while the distal region is composed of strands and presents a flexible bending stiffness. An intermediate region of relatively short length where the cable attaches to the upper portion has a bending modulus that changes quickly from fairly stiff to flexible. The location of this portion may be varied by changing the relative lengths of the proximal solid and distal cable portions thus determining or limiting to a small local region the area of bone which may experience any stress shielding. The stiffness of the cable may also be varied by use of different gauge wires or the addition of welds or circumferential bands. In this variable modulus prosthesis hip stem the stiffness at the proximal end is high compared to natural bone and acts as a load-bearing member. The stiffness at the distal end is low compared to natural bone, allowing the natural bone to participate in bone support. The variable modulus prosthetic hip stem does not have similar modulus or stiffness to a natural bone at any section of the prosthetic hip stem, but merely supports loads locally at different locations along the length of the hip stem.

U.S. Pat. No. 6,312,473 to Oshida discloses an orthopedic implant system. This orthopedic implant system satisfies the biological, mechanical and morphological compatibility needs. A solid metal femoral stem and a solid metal acetabular head are at least partially covered with diffusion-bonded foamed-shaped sheet made of commercially pure titanium or titanium alloy(s). The open-cells in said foamed metal sheet are impregnated with biocompatible polymethyl methacrylate resin cement, which is reinforced with selected oxides including alumina, magnesia, zirconia, or a combination of these oxides along with an application of a small amount of a metal primer agent. This disclosure mainly covers an aluminum foam, which is available and projects properties of a titanium foam, which is said to be currently unavailable. The disclosure projects the strength, and the modulus of elasticity of the foam layer would be less than that of a bone and would require reinforcement by a biocompatible polymer such as PMMA. Since the foam is projected to be the weakest element, the orthopedic implant is not securely attached to the bone structure even when bone ingrowth occurs within the bone. Therefore, the orthopedic implant will experience movement under load, creating a dangerous situation.

U.S. Pat. No. 6,656,226 to Yoon discloses a plastic jacket for a cementless artificial joint stem and artificial joint having the jacket. The artificial joint pivotally connects a first bone to a second bone. A hole is formed in the second bone into which the artificial joint is inserted. The artificial joint comprises a head that connects with the first bone, a stem of a longitudinal length to fit into the hole of the second bone, a neck connecting the head to the stem and a jacket enclosing the stem. The jacket comprises an outer surface and a porous body. The body is inserted into the hole of the second bone so that substantially the entire outer surface of the jacket is in direct contact with inner walls of the hole. The jacket has a blind opening that receives most of the stem. The body of the jacket comprises a plastic material, and the outer surface of the body is rough, such that the jacket is adapted to adhere to the second bone by natural growth of the second bone onto the outer surface of the jacket without use of cement between the outer surface of the jacket and the inner walls of the second bone. This cementless artificial joint implant has a porous or rough plastic jacket, which slides over the metallic stem and is inserted into a hole in the second bone. The bone tissue is expected to grow into the rough porous external surface of the plastic jacket. Thus, the plastic with bone ingrowth may be retained by the bone tissue in time, but there is no attachment between the metallic stem and the plastic jacket, as a result, the overall cementless fixation only relies on the friction between the plastic jacket and the metallic stem for implant integrity.

U.S. Pat. No. 6,887,278 to Lewallen discloses a prosthetic implant having a segmented flexible stem exhibiting varying stiffness. The stem comprises an elongated core and segments extending outward from the core. The segments are spaced apart so as to define transverse grooves surrounding the core between adjacent segments. The longitudinal length of the grooves, and the microstructurally consistent implant materials used for the core and the segments are selected such that the stiffness of the stem varies from the proximal end to the distal end. Typically, the stiffness of the stem will be lower at the distal end such that the distal end of the stem bears less force when loaded and thereby transfers more load to the proximal end of the stem, which has a higher stiffness. As a result, stress shielding the load carried by the implant bypasses the proximal end of the stem and minimizes bone resorption adjacent the proximal end of the stem. It is therefore an advantage of the prosthetic implant is to provide a fixation stem with reduced or varying stiffness such that the stress shielding problems associated with the high mechanical stiffness of the stem can be minimized. In this segmented flexible stem the central core of the femur implant is provided with a series of tubular sections, which result in segments that are separated by a groove. The grooves reduce the stiffness of the femur implant. Optionally, the femur implant may be coated with a porous metallic layer to enhance bone bonding properties. In spite of the presence of segments and grooves, the overall stiffness of the femur implant is still very high compared to the stiffness of a bone tissue. In addition, the presence of grooves decreases the load carrying capacity of the femoral implant.

U.S. Pat. No. 6,913,623 to Zhu discloses a two-piece fused femoral hip stem. The two-piece femoral stem orthopedic implant includes a metal core having a first end, a second end, a first elastic modulus, and a first porosity. A proximal body is fused directly onto the metal core between the first and second ends. The proximal body has a second elastic modulus, which is less than the first elastic modulus, and a second porosity, which is greater than the first porosity. The porosity of the proximal body may vary throughout. The orthopedic implant minimizes the elastic modulus mismatch between the femoral stem and the surrounding bone material. To this end, a metal core has a first end, a second end, and a first elastic modulus.

The metal core has a proximal body between the first end and the second end, the proximal body has a second elastic modulus which is less than the first elastic modulus. In this two-piece fused femoral stem the proximal porous body is said to have a lower elastic modulus and contacts the surrounding bone only in the proximal portion of the implant. In the distal end of the metallic core, no porous body is provided and therefore, there is direct contact between metal core and bone tissue. This significant mismatch in elastic modulus at the distal section takes away any benefit of reduced elastic modulus at the porous proximal section. This implantable prosthesis uses a metallic core with an inserted polymeric proximal body having elastic modulus similar to bone tissue. However, the bond between the polymeric proximal body and the metallic core may be inadequate to produce a successful orthopedic implant.

There remains a need in the art for femoral stems for canines or humans that are compliant with the stiffness and elastic modulus of bone tissue so that load is transferred between the bone and the implant without creation of bone separation or crack formation. When stiffness mismatch is present, the same load carried elongates the implant member differently than the bone tissue resulting in crack formation or implant separation. Needed in the art is a compliant elastic stiffness or modulus femoral stem for canines or humans that will provide load transfer without crack formation from the initial time period immediately after implant surgery to complete healing of implanted tissue by bone ingrowth. It would be particularly advantageous if, due to the intimate contact between the prepared bone and the bone compliant femoral stem during the healing period, a long term permanent bond between the implant and the underlying bone structure could be made possible, so that extended motion meeting the needs of a dog could be provided. It would also be advantageous if the implanted device were to function without corrosion or rejection reactions throughout the lifetime of the dog or human patient, since the implanted device is permanently placed within the bone structure.

SUMMARY OF THE INVENTION

The present invention provides a canine femoral stem that is compliant with the stiffness and elastic modulus of bone tissue, so that load is transferred between the bone and the implant without creation of bone separation or crack formation. The compliant elastic stiffness or modulus of the canine femoral stem provides load transfer without crack formation from the initial time period immediately after implant surgery to complete healing of implanted tissue by bone ingrowth. Due to the intimate contact between the prepared bone and the bone compliant canine femoral stem during the healing period, a long term permanent bond between the implant and the underlying bone structure is made possible, so that extended motion meeting the needs of a dog is provided. Once implanted, the device functions without corrosion or rejection reactions throughout the lifetime of the dog.

In one aspect, the bone-compliant canine femoral stem has external surfaces that are compatible with natural bone with respect to biocompatibility and elastic modulus. The external bone contacting surfaces of the canine femoral stem have a modulus substantially similar to that of a natural bone. The external surface of the bone-compliant femoral stem uses a biocompatible titanium core, having a thick porous titanium surface on the upper portion and a bioresorbable polymeric or calcium triglyceride bone cement material.

Generally stated, the bone-compliant canine femoral stem comprises: (i) a titanium core, (ii) a substantially thick fully-porous proximal titanium body, and (iii) a distal section of a bioresorbable material with a modulus close to that of cancellous bone. The Femoral Stem addresses the issues of stress mismatch by providing materials in different proportions within the construct which result in a modulus for the stem at the bone contacting interface that is closer to the modulus of the proximal and distal femur. This objective is achieved through implant geometry and material selection.

The Femoral Stem incorporates a titanium core (could also be cobalt chrome or another biocompatible metal), a proximal titanium body, which is fully porous and thick, and a distal section of a bioresorbable material with a modulus close to cancellous bone. The proximal body, which is fully porous, provides the appropriate pore sizes to allow for bone ingrowth. Because of its fully porous nature and the layer thickness of 0.080 to 0.120 inches, the proximal body yields under low load and creates a modulus that is similar to a bone tissue. This thickness geometry in combination with porous titanium material cooperate to bring the modulus of the porous titanium in contact with the bone tissue to a modulus closer to that of bone. The biocompatible porous metallic body is composed of sintered beads of metal, including titanium, titanium alloy or chromium alloy. The porous metallic body may also be made from titanium fiber metal.

Our present invention provides a bone-compliant canine femoral stem, which is characterized by having modulus at the bone-contacting surface matching that of the natural bone, enabling load transfer without formation of cracks at the interface. The low modulus in the bone contact region of the upper portion of the canine femoral stem is formed by a thick titanium porous body diffusion bonded or mechanically attached to a central solid metallic core body. This low modulus is due to inclusion of multiple levels of porosity, which results in large movement at low loads or an effective elastic modulus, which is small. At the region of the porous body which contacts the titanium central core, the modulus is lesser than that of titanium, but is much larger than that of the porous body at the bone contacting region. The modulus falls rapidly in a progressively decreasing fashion along the thickness of the porous titanium body as a function of distance from the titanium central core.

In the lower portion of the bone-complaint canine femoral stem, a thick low modulus biosorbable contact region is provided that is manufactured by compression molding of bio-compliant polymer such as PEEK or calcium triglyceride bone cement over the central solid metallic core. The modulus of the biocompatible polymer or the calcium triglyceride bone cement is naturally similar to that of bone tissue and therefore no porosity is needed to be bone-compatible.

When the bone compliant canine femoral stem is inserted into a surgically prepared bone cavity, the lower portion of the bone compliant femoral stem is firmly fitted into the cavity providing initial stability immediately after surgery. The bone ingrowth occurs both in the lower and upper portion of the bone-complaint canine femoral stem since the overall elastic modulus of the diffusion bonded or mechanically attached porous body and the compression or injection molded lower portion is very similar to the bone tissue. The load is therefore transferred from the central solid metallic core to the bone tissue without creating delamination or crack formation at the bone contacting regions of the bone-compliant canine femoral stem.

The bone-compliant canine femoral stem is manufactured by using one of several processes. In a first process, there is selected a central titanium core, which is slender and tapered.

The slender titanium core is reinforced and rigidized by having flanges extending along its length to provide a cross section that is similar to a double L beam. This structure is light and yet supports bending loads effectively. A separate porous titanium body matching the shape of the titanium central core is formed by diffusion bonding of titanium beads. This porous titanium body may have sufficient length to cover the entire length of the titanium central core or may be of a length sufficient to cover only the proximal portion of the bone-compliant canine femoral stem. In a next step of the process, the titanium porous sintered body is metallurgically bonded to the titanium central core by diffusion bonding.

The distal portion of the bone-compliant femoral stem which may be covered with a porous titanium body or which may be bare titanium core is compression or injection molded with a bio-compatible polymer such as PEEK. This may be done by direct compression or injection molding of the polymeric body or first molding the polymeric body separately and heating it to compression or injection mold the polymeric body over the distal portion of the bone compatible canine femoral stem. Alternately, a bone-compatible calcium triglyceride bone cement may be used to coat a thick layer over the bare or porous titanium body covered titanium core at the distal portion of the bone-compliant canine femoral stem.

BRIEF DESCRIPTION OF DRAWINGS

The invention will be more fully understood and further advantages will become apparent when reference is had to the following detailed description and the accompanying drawings, in which:

FIG. 3a is a cross sectional view of the bone compliant canine femoral stem;

FIG. 3b is a graph depicting on opposed coordinates the modulus of the bone-compliant femoral stem in the porous titanium body as a function of distance from the titanium core;

DESCRIPTION OF THE PREFERRED EMBODIMENTS

Figure 1:
FIG. 1 is a side elevation illustrating a traditional canine femoral stem.
Figure 1:
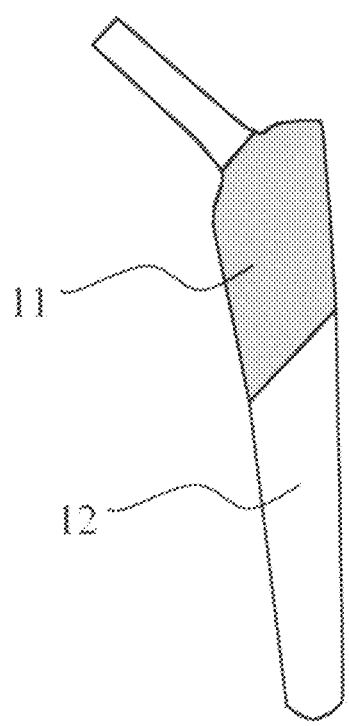

This invention relates to a bone-compliant femoral stem which may be attached using cement or by way of a cementless procedure. The bone-compliant femoral stem is herein described with particular reference to use in canines. However, it will be understood that the principles of the invention are fully applicable to use of the femoral stem in humans. The bone-compliant canine femoral stem comprises a slender biocompatible metallic support member made from a Ti alloy, preferably Ti—Al—V alloy or a chromium alloy. The dimensions of the slender metallic body are generally much less than the surgically prepared bone cavity and are of a size sufficient to withstand the stresses provided by a canine patient immediately after a surgical procedure. The slender metallic support member is completely surrounded in the proximal and distal region by a porous biocompatible member, preferably a titanium member, which is diffusion bonded or mechanically attached to the slender metallic support member. This diffusion bonding results in metallurgical permanent bonding of the porous metallic member to the metallic supporting member. In traumas involving fractures of bone and in osteotomies of bone, in order to re-orient alignment between bone segments, bone plates and screws have been used for many decades. They are used at the fracture/osteotomy site to stabilize the segments of bone and to allow the normal healing process to take place. Stabilizing the bone segments is critical to the healing process in order to avoid non-union that can be caused by micro motion between the bone segments.

Typically titanium and its alloys have an elastic modulus of 110 GPa and cobalt chromium alloys have an elastic modulus of 205 GPa while a cortical bone has a modulus of 15 GPa. A cancellous bone has a modulus of only 0.8 GPA. As a result, both titanium alloy and cobalt chromium alloys have a modulus that far exceeds the modulus of the bone with which the metallic support member is supposed to bond. When a load is applied to the bonded bone and to a metallic object, the load is primarily borne by the metallic member and creates a minimal deflection. On the other hand, the bone tissue takes a very small amount of load and is extended to the same strain value or displacement. This gross difference in elastic modulus results in shear forces at the bone-metallic object interface causing separation and delamination at this interface, which interferes with the bone healing process and attachment of the bone to the metallic object. A porous metallic structure, depending on how it is made, has an elastic modulus in the range of 3.5 GPa to 8 GPa which is closer to the modulus of the bone than the titanium alloys or cobalt chromium alloys. The titanium alloy or the cobalt chromium alloy is diffusion bonded or mechanically attached to the porous metallic medium. Since this bond is a metallurgical bond, the elastic modulus decreases rapidly as a function of distance from the porous metal medium-metallic support medium interface along the porous metallic medium. Within a very short distance, typically 50 to 100 microns the modulus approaches the native elastic modulus value of the unattached porous metallic medium. The porous metallic medium is provided at such a thickness that the modulus of the porous metallic medium is close to its native value, which is very close to the modulus of a native bone. Therefore, when the canine femoral member is subjected to load, the metallic support member supports most of the load, and extends its length with a specific strain value according to the high elastic modulus. The metallurgically attached porous metallic member extends to the same extent and the same strain level and load shared by the porous metallic member is only equal to the strain multiplied by the porous metallic member's elastic modulus. Since the elastic modulus decreases rapidly as a function of distance from the metallic support member within the porous metallic member, the load carried also decreases rapidly. At the bone-contacting surface of the porous metallic member, which is further away from the interface with the metallic support member, the same strain results in a much smaller load. As a result, bone ingrowth can occur without the possibility of delamination.

FIG. 1 illustrates at 10 an illustration of the prior art traditional canine femoral stem made from cobalt chromium alloy. The porous surface coating is applied only to the proximal body portion of the stem as shown at 11. The porous portion is built by sintering of layers of beads of cobalt chromium or titanium to a depth of only 0.030 inches. The distal portion of the stem shown at 12 is a solid non-porous stem, typically a cobalt-chromium alloy. The porous body made from sintered beads is not compliant due to its small thickness and cannot function by crushing to provide intimate contact with a surgically prepared bone cavity. The thickness of this layer is insufficient to reduce the high modulus of the cobalt chromium stem at the bone-contacting interface. There is no porous coating at the distal end to facilitate bone ingrowth.

Figure 2:
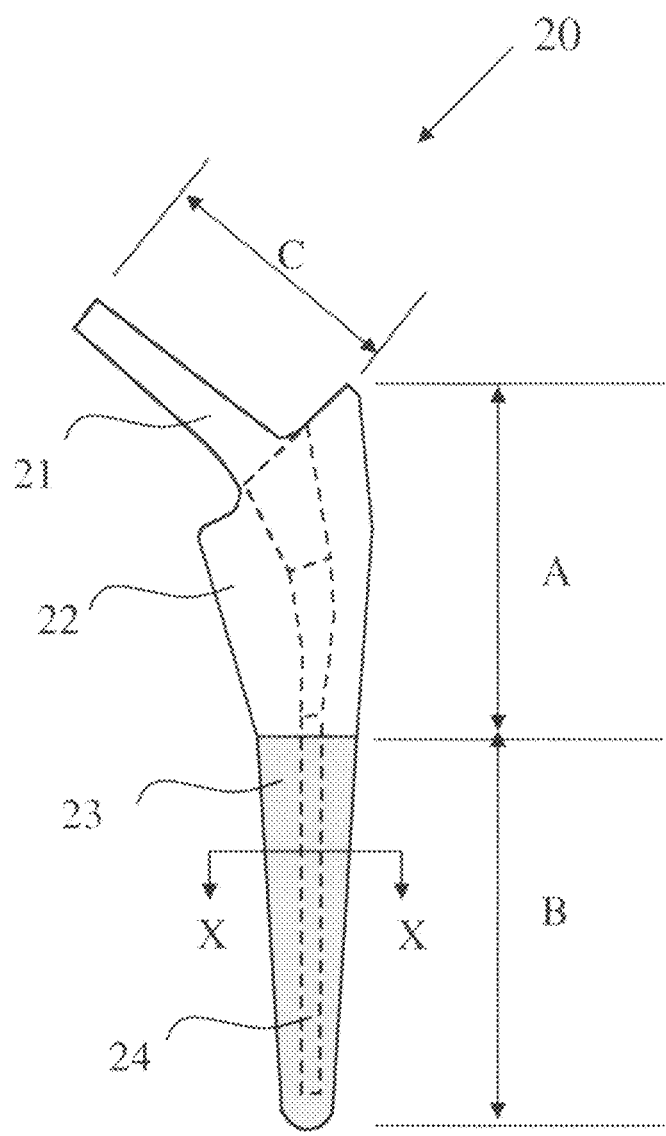
FIG. 2 is a side elevation illustrating design features of a bone-compliant canine femoral stem.

FIG. 2 illustrates the design features of a bone-compliant canine femoral stem generally shown at 20. The bone-compliant canine femoral stem has a body area or metaphysical area A, a distal area or diaphysical area B and a neck area C. The bone-compliant canine femoral stem has a titanium alloy or cobalt chromium metallic support core 21, over which a fully porous titanium body 22 is diffusion bonded or mechanically attached. The diffusion bonded or mechanically attached porous metallic member extends and covers the metaphysical area A and disphysical area B. The disphysical area B is coated with a biosorbable material 23. The titanium core as shown at 24 is a one-piece metallic support core which extends from the neck portion to the body and distal portion.

FIG. 3a illustrates at 30 the cross section and relative dimensions of the bone-compliant canine femoral stem along XX of FIG. 2. The cross section shows the yellow colored metal (titanium) supporting core at 31 marked as X and the green colored porous metallic (titanium) body marked as Y at 32. The thickness of the porous metallic body has a thickness of at least 0.080 inches, a dimension comparable to the titanium core dimension. The orange colored region is the typical bone ingrowth region. The FIG. 3b diagrammatically shows in the insert figure illustrating the elastic modulus as a function of distance from the central titanium central core interface.

Figure 4A:
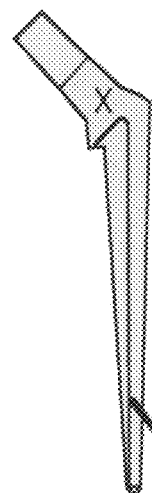
FIG. 4a through 4h illustrate a process for manufacturing the bone-compliant canine femoral stem
Figure 4B:
Figure 4C:
Figure 4F:
Figure 4D:
Figure 4E:
Figure 4G:
Figure 4H:
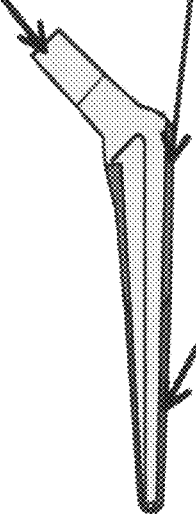

FIGS. 4a through 4h illustrate the various components of the bone-compliant canine femoral stem and its manufacturing process. FIG. 4a shows the front view of the solid titanium metal core shown in yellow color. FIG. 4b shows its side view indicating its complex geometry. FIG. 4c shows in green the sintered porous titanium alloy body constructed by diffusion bonding of spheres of titanium. It has a central aperture as shown. FIG. 4d shows the front view of the porous titanium body while FIG. 4e shows its side view. FIG. 4f shows in blue a biocompatible polymeric body with a central aperture. FIG. 4g shows the front view of the biocompatible polymeric body. FIG. 4h exemplifies the method of assembly of the bone-compliant canine femoral stem. The sintered porous titanium body 4b is slipped over the central solid core 4a and diffusion bonded in a furnace or mechanically attached to create a metallurgical bond between the porous titanium body and the solid metallic core. The sintered component is cooled and the molded polymeric component 4g is slipped over the distal end and is subjected to compression molding. The bone-compliant canine femoral stem thus produced is illustrated in 4h.

In an alternate embodiment, the porous titanium body may be sintered to the central titanium core directly by diffusion bonding or sintering. The distal portion of the central titanium core may be molded with bio-compatible polymer such as PEEK by compression molding or injection molding. As an alternate, the distal portion may be provided with a thick coating of calcium triglyceride bone cement, which is inherently porous.

The salient features of the Bone-Compliant Canine Femoral Stem include:

1. a slender titanium core having a proximal geometry (neck) allowing for the attachment of a femoral head;
2. the slender titanium core having a taper from the neck area into a curved conical area providing strength for hip biomechanics and being of sufficient size to have a proximal body added;
3. the slender titanium core having a thick porous titanium metal body diffusion bonded or mechanically attached throughout substantially its entire or proximal length;
4. the diffusion bonding creating permanent metallurgical attachment between the titanium core and the porous metallic body;
5. the porous metallic body having an elastic modulus and mechanical properties similar to a natural bone and the diffusion bond gradually decrementing the elastic modulus of the titanium core to that of the porous metallic body from the titanium core-porous metallic body interface and reaching the native elastic modulus of the porous metallic body within a very short distance along the thickness from the interface;
6. the thick porous metallic body when it makes contact with a bone tissue providing a bone-complaint contact with the bone since the elastic modulus has been decremented sufficiently due to the thickness of the porous metallic body;
7. the distal section of the slender titanium core with or without the thick porous titanium body is coated with and by a moldable biosorbable polymer or ceramic coating;
8. the proximal portion of the canine femoral stem comprising a thick porous metal body bonded to a slender titanium core press fitting tightly into a surgically prepared bone cavity and providing initial stability in both cemented and cementless surgical procedures;
9. the biosorbable polymer or ceramic coating in the distal section of the bone-compliant canine femoral stem encouraging bone ingrowth into the porous metallic body surrounding and being bonded to the slender titanium core, thereby promoting rapid stability of the implanted canine femoral stem;
10. the proximal portion of the canine femoral stem that is not coated with moldable biosorbable polymer or ceramic coating experiencing substantial bone ingrowth over time;
11. the slender titanium core with bone ingrown porous metallic body and biosorbable polymer or ceramic coating sharing load carrying capability together with the natural bone;
12. the bone-compliant canine femoral stem having improved initial fixation and providing more consistent bone ingrowth owing to a stiffness similar to the bone and thereby moving with the bone under physiological loads as opposed to stiffer constructs which would have more relative motion with the bone interfaces due to the relative stiffness mismatch;
13. a stem design, which allows for the preparation of the canine femoral canal by a sequential broaching method or a combination of tapered reamers and broaches; and
14. a sufficient number of stem sizes to provide initial press fit to a wide range of canine femorae.

Having thus described the invention in rather full detail, it will be understood that such detail need not be strictly adhered to, but that additional changes and modifications may suggest themselves to one skilled in the art. For example, the porous body can comprise a three-dimensional, porous metal foam manufactured from biocompatible material such as titanium, tantalum, cobalt-chrome, niobium or the like. Such a piece of foam-metal can have flexural and strength properties compatible with the bone structure. These modifications are intended to fall within the scope of the invention as defined by the subjoined claims.

What is claimed is:

1. A femoral stem, comprising:
a central solid slender metal core having a neck of the stem with geometry allowing for the attachment of a femoral head, a proximal core body of the stem and a distal core body of the stem;
a thick porous titanium body having a central aperture matching the shape of said proximal core body of the stem, the thick porous titanium body being diffusion bonded or mechanically attached directly onto the proximal and distal core bodies; the titanium body exhibits elastic modulus matching that of bone tissue at a bone contacting external surface and encourages bone ingrowth, providing a bone compliant femoral stem proximal region; and
a biocompatible ceramic body coating only the distal core body of the femoral stem with the biocompatible ceramic body coating an end of the distal region of the central core and a circumferential surface of the distal region of the central core; the biocompatible ceramic body exhibiting elastic modulus matching that of bone tissue, providing a bone compliant femoral stem distal region;
whereby an interface between the bone tissue and an external surface of the femoral stem proximal and distal regions is prevented from delamination of crack formation due to the bone compliant property of the femoral stem.

2. The femoral stem of claim 1, wherein the porous titanium body has a thickness in the range of 0.080 inches to 0.120 inches.

3. A The femoral stem of claim 1, being appointed for use in humans.

4. A The femoral stem of claim 1, being appointed for use in canines.

5. The femoral stem of claim 1, wherein the biocompatible ceramic body coating the distal region of the central core is composed of calcium triglyceride bone cement.

6. The femoral stem of claim 1, wherein the biocompatible ceramic body has a thickness in the range of 0.080 to 0.120 inches.

7. A femoral stem, comprising:
a central solid slender metal core having a neck of the stem with geometry allowing for the attachment of a femoral head, a proximal core body of the stem and a distal core body of the stem;
a thick porous titanium body having a central aperture matching the shape of the proximal core body of the stem, the thick porous titanium body being diffusion bonded or mechanically attached to a proximal portion of the central core; the titanium body exhibits elastic modulus matching that of bone tissue at a bone contacting external surface and encourages bone ingrowth, providing a bone compliant femoral stem proximal region;
a biocompatible ceramic body coating only the distal core body of the femoral stem, the biocompatible ceramic body coating surrounding a circumferential surface of the distal region of the central core; the biocompatible ceramic body exhibiting elastic modulus matching that of bone tissue, providing a bone compliant femoral stem distal region; and
the biocompatible ceramic body having a thickness in the range of 0.080 to 0.120 inches; and
whereby an interface between the bone tissue and an external surface of the femoral stem proximal and distal regions is prevented from delamination of crack formation due to the bone compliant property of the femoral stem.

8. The femoral stem of claim 7, wherein the biocompatible ceramic body coating the distal region of the central core is composed of calcium triglyceride bone cement.

* * * * *